United States Patent [19]

Neftel et al.

[11] Patent Number: 5,782,611
[45] Date of Patent: Jul. 21, 1998

[54] PORTABLE PUMP ASSEMBLY

[76] Inventors: Frédéric Neftel, 17 Rue des Terreaux, CP82, CH1000 Lausanne 9, Switzerland; Bernard Bouvier, 17 Rue de la Marne, 95610 Eragny sur Oise, France

[21] Appl. No.: 817,545

[22] PCT Filed: Oct. 6, 1995

[86] PCT No.: PCT/FR95/01034

§ 371 Date: Apr. 4, 1997

§ 102(e) Date: Apr. 4, 1997

[87] PCT Pub. No.: WO96/11025

PCT Pub. Date: Apr. 18, 1996

[30] Foreign Application Priority Data

Oct. 6, 1994 [FR] France ................... 94 11943

[51] Int. Cl.⁶ .......................... F04B 53/00; F04B 43/08
[52] U.S. Cl. .............................. 417/234; 417/313
[58] Field of Search ........................ 417/313, 360, 417/234, 477.1; 248/225.11, 223.41, 222.11; 604/153

[56] References Cited

U.S. PATENT DOCUMENTS

| | | | |
|---|---|---|---|
| 4,844,397 | 7/1989 | Skakoon et al. | 248/231 |
| 5,080,310 | 1/1992 | Choi | 248/222.11 |
| 5,168,892 | 12/1992 | Sunderland | 417/360 |
| 5,170,817 | 12/1992 | Sunderland | 417/360 |
| 5,236,004 | 8/1993 | Sunderland et al. | 417/360 |
| 5,472,317 | 12/1995 | Field et al. | 417/234 |
| 5,478,211 | 12/1995 | Dominiak et al. | 417/234 |
| 5,482,446 | 1/1996 | Williamson et al. | 417/474 |

FOREIGN PATENT DOCUMENTS

| | | | |
|---|---|---|---|
| WO 91 19523 | 12/1991 | WIPO | A61M 5/142 |
| WO 93 10835 | 6/1993 | WIPO | A61M 5/172 |

OTHER PUBLICATIONS

International Search Report for PCT/FR95/01304, filed Oct. 6, 1995.

*Primary Examiner*—Charles G. Freay
*Assistant Examiner*—Peter G. Korytnyk
*Attorney, Agent, or Firm*—Wolf, Greenfield & Sacks, P.C.

[57] ABSTRACT

A portable pump assembly is provided. The pump assembly includes a pump and various accessories that enable the pump or alternatively, the pump and a pouch containing a liquid for injection, to be fixed to various accessories without requiring modification of the pump box and without requiring specific fixing apparatus for each of the accessories used with the pump.

10 Claims, 4 Drawing Sheets

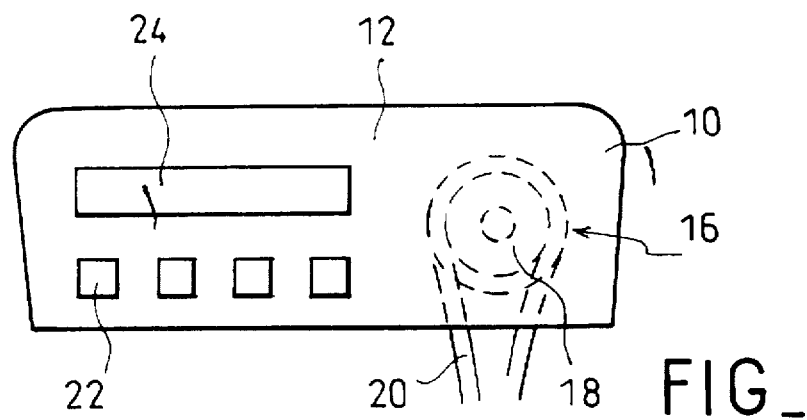
FIG_1
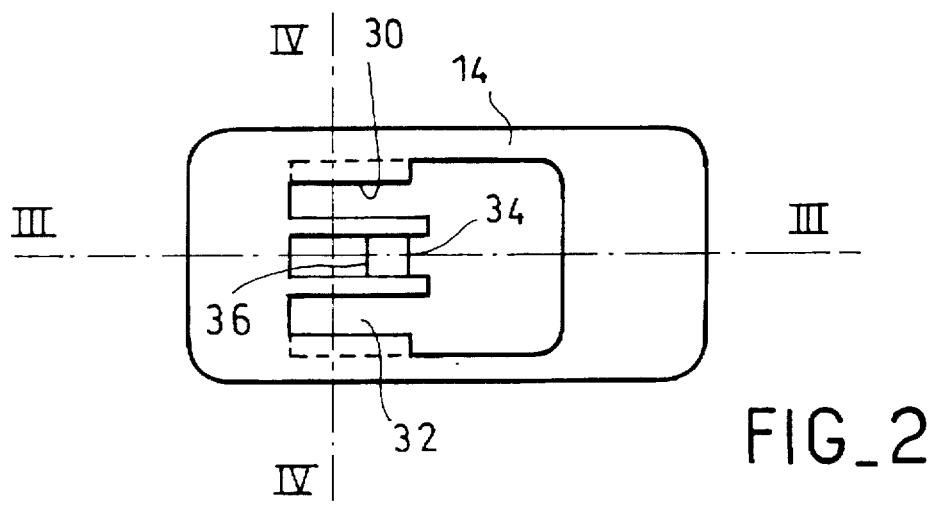
FIG_2
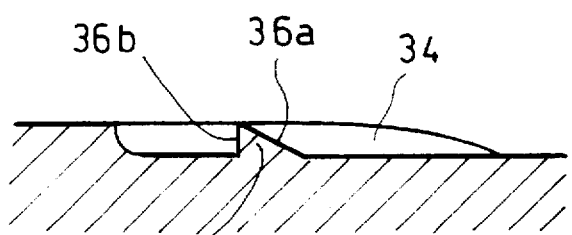
FIG_3
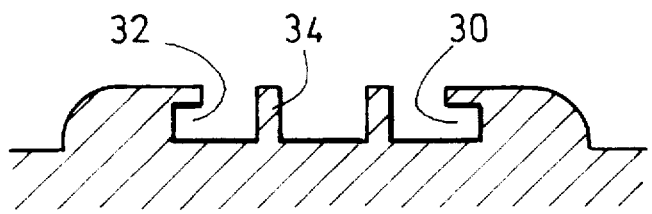
FIG_4

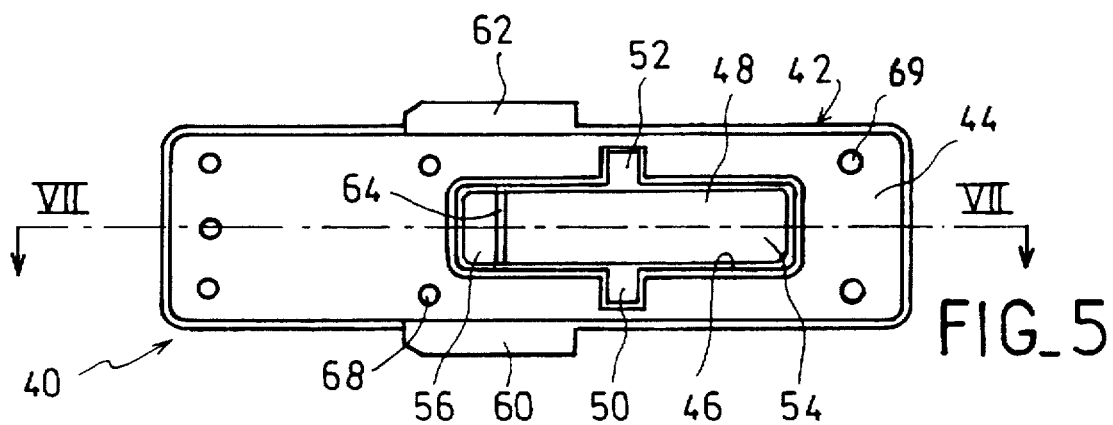
FIG_5
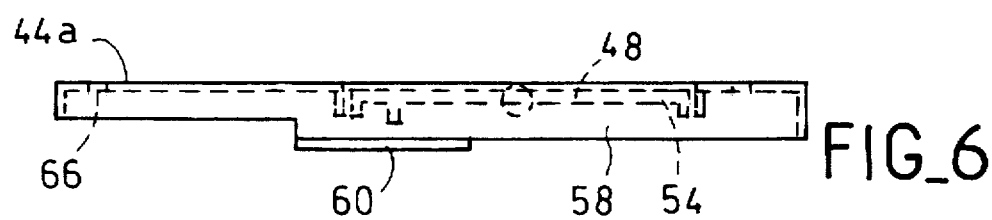
FIG_6
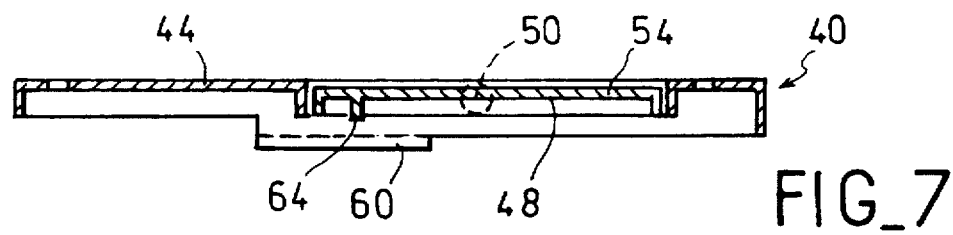
FIG_7
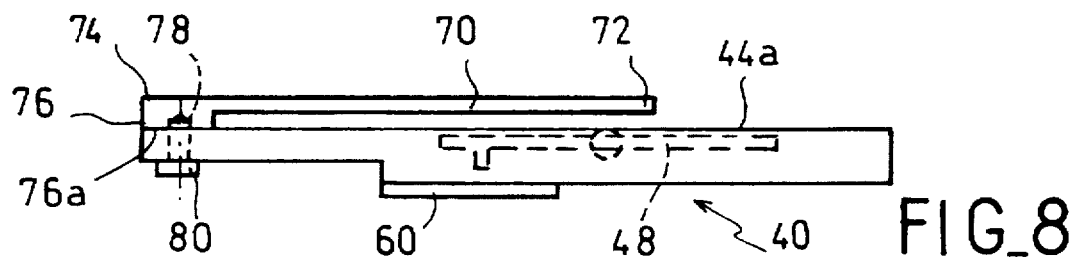
FIG_8
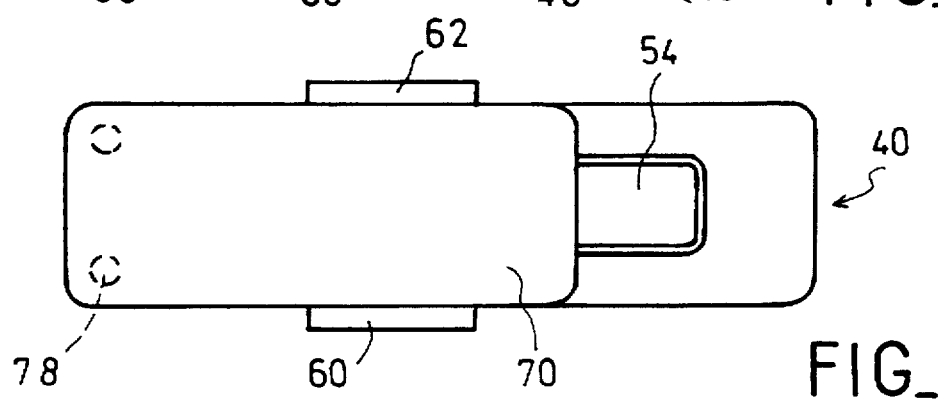
FIG_9

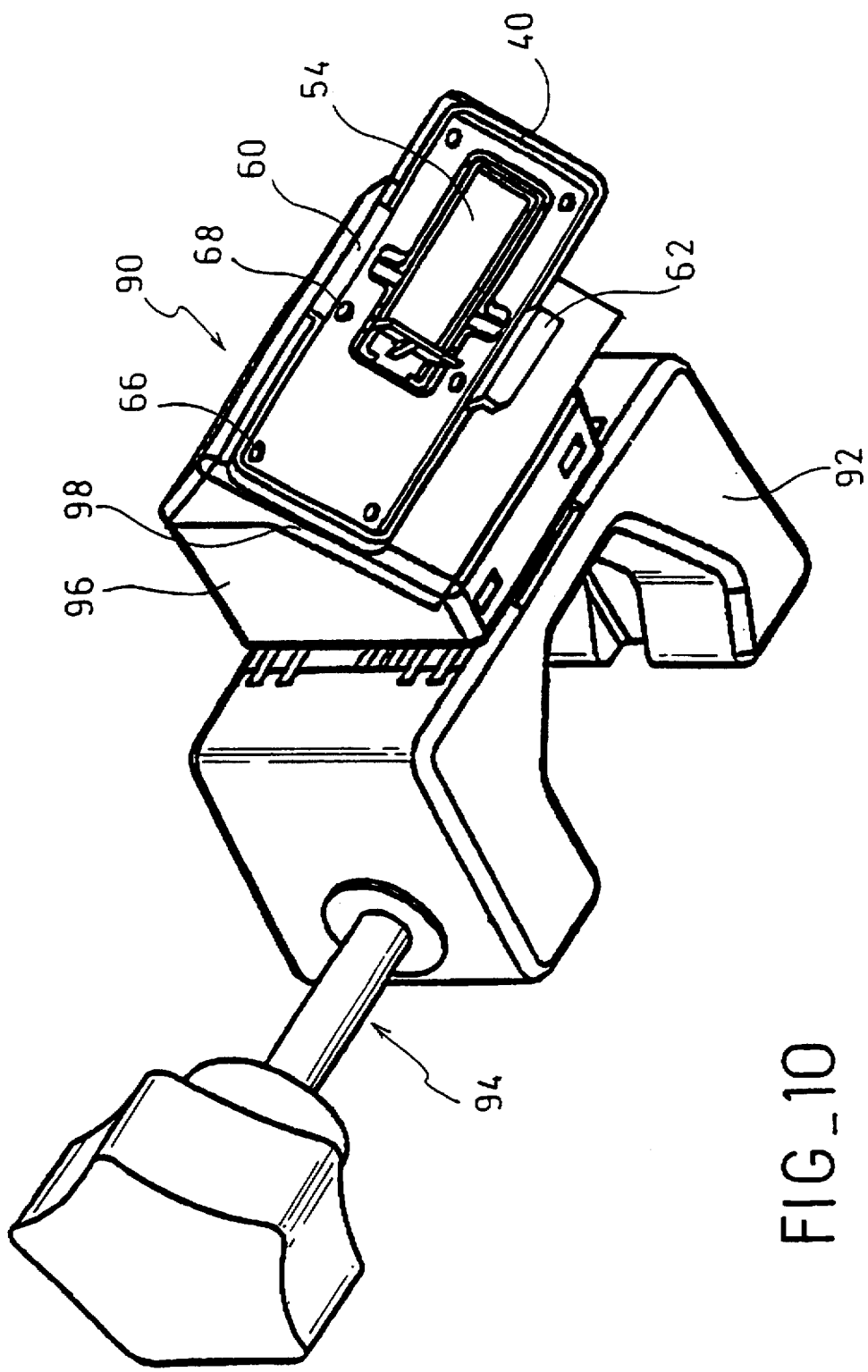
FIG_10

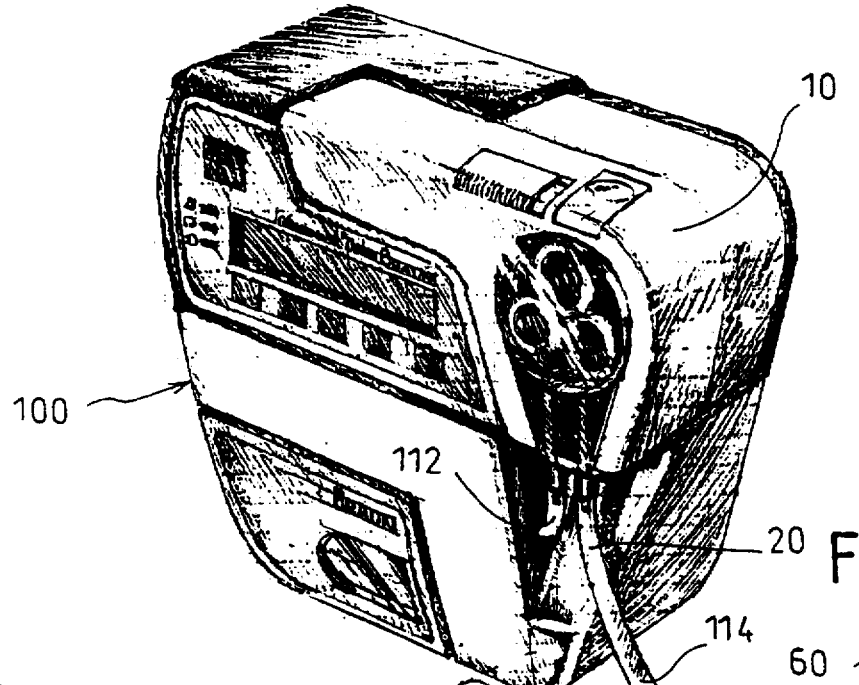
FIG_13
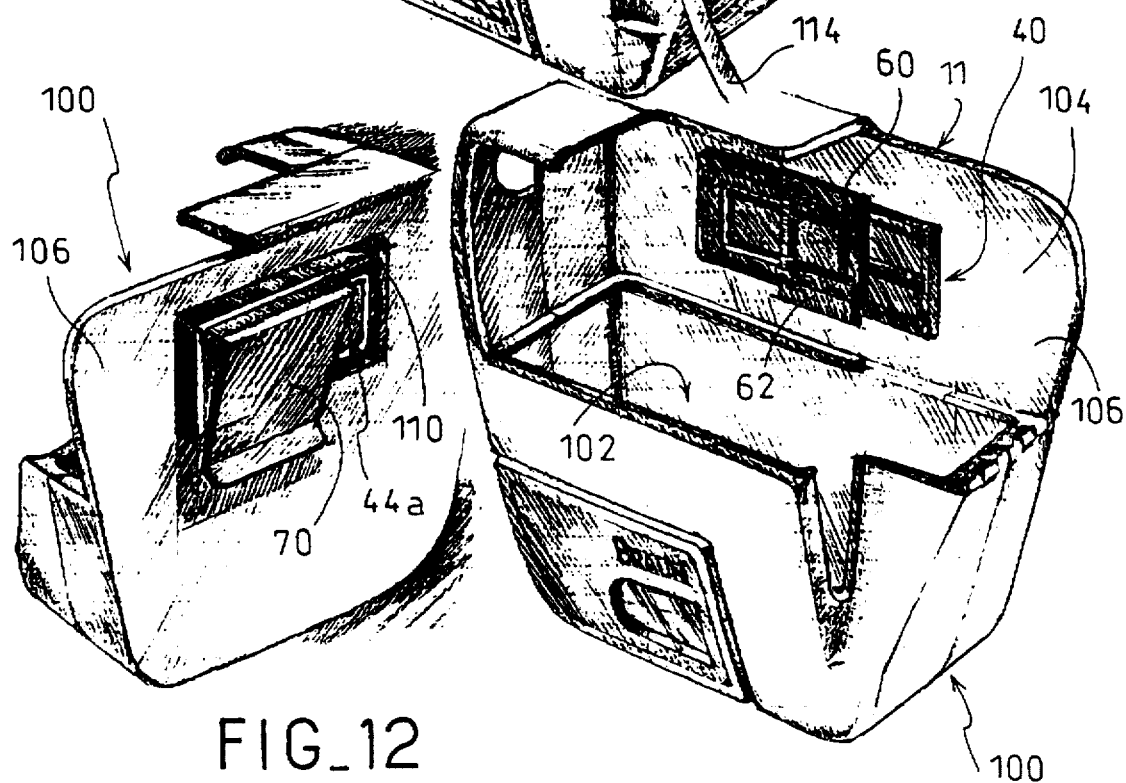
FIG_12 FIG_11

PORTABLE PUMP ASSEMBLY

BACKGROUND OF THE INVENTION

The present invention relates to a portable pump assembly.

More precisely, the invention relates to a portable pump comprising a pump proper mounted in a box, and a plurality of accessories that can be fixed on said pump box.

In the medical and hospital fields, ever increasing use is being made of small-sized pumps, in particular of the peristaltic type, for delivering medical or physiological serums to patients. These pumps serve to displace various liquids within a flexible hose having one end connected via a cannula or a needle to the patient, with the rate at which liquid is injected being under very accurate control. Usually such pumps are in the form of a box containing both the mechanical portion of the pump and its electronic control circuits together with an electrical power supply. A keypad is provided on the front face of the pump for programming operation of the pump and also various indications.

The pump can be used in various situations. It may serve to dispense liquid to a patient confined to a hospital bed. Under such circumstances, it is desirable to be able to fix the pump on a bracket that may itself also support the flask of liquid that is to be dispensed. In other cases, the pump is worn continuously by the patient. In this situation, either the pump needs to be fixed to a belt worn by the patient for reasons of convenience, said belt itself carrying a pouch containing the liquid to be injected, or else in other circumstances the pouch is contained in a case that forms a kind of bag, and it is then desirable to be able to associate the pump with the bag containing the pouch of liquid.

OBJECT AND SUMMARY OF THE INVENTION

An object of the present invention is to provide a portable pump assembly in which the pump can be associated with various accessories enabling the pump to be fixed and/or the pump and the pouch containing the liquid for injection to be fixed. It is also desirable for the pump to be capable of being conveniently fixed to said various accessories without needing to modify the pump box and without having to use specific fixing means for each of the accessories used with the pump.

To achieve this object, according to the invention, the portable pump assembly which comprises a pump mounted in a box and a plurality of distinct accessories fixable on said pump box, is characterized:

in that said pump box has both a control face and a fixing face that is distinct from the control face, said fixing face including first mechanical fixing means and non-moving first locking means;

in that it further includes a single link member having a first face and a second face, the first face being provided both with second mechanical fixing means, said first and second mechanical fixing means forming a rib-and-slideway system, and with moving second locking means such that when the first and second mechanical fixing means co-operate mutually, the first and second locking means also co-operate to secure said link member on said box, and the second face including a first fixing zone and a manual control element for unlocking the second locking means;

in that each accessory includes a second fixing zone suitable for engaging at least a portion of said first fixing zone; and in that it further includes fixing means for fixing said second fixing zone on at least a portion of said first fixing zone.

It will thus be understood that by means of the invention it is possible, by making use of the link member which is always of the same shape, to fix an accessory on the fixing face of the pump box. The fixing face of the pump includes special means for enabling the link member to be fixed and locked or unlocked, while the link member itself includes standard means for fixing to the accessory that is to be secured to the pump.

BRIEF DESCRIPTION OF THE DRAWINGS

Other characteristics and advantages of the present invention appear more clearly on reading the following description of various embodiments of the invention, given as non-limiting examples. The invention refers to the accompanying drawings, in which:

FIG. 1 is a view of the front face of the box for a pump;

FIG. 2 is a view of the fixing back face of the pump box;

FIG. 3 is a fragmentary section on line III—III of FIG. 2;

FIG. 4 is a fragmentary section view on line IV—IV of FIG. 2;

FIG. 5 is a view from beneath of the link member;

FIG. 6 is a side view of the link member;

FIG. 7 is a section view on line VII—VII of FIG. 5;

FIG. 8 is a side view of the link member fitted with a first accessory that forms a hook;

FIG. 9 is a view similar to FIG. 8 but as seen from above;

FIG. 10 is a perspective view of a second accessory that can be fixed on the pump and that consists in a piece for fixing to a bracket; and FIGS. 11 to 13 are perspective views of another accessory fixable to the pump and consisting in an case for containing the liquid to be injected by means of the pump.

DETAILED DESCRIPTION

With reference initially to FIGS. 1 to 4, there follows a description of an example of a pump, and in particular a peristaltic pump, suitable for use in the invention. The pump comprises an outer box 10 of generally rectangular shape having a control front face 12 and a fixing back face 14. Inside the box, there are to be found essentially a peristaltic pump 16 of conventional type including rotary wheels that co-operate with a deformable tube 20 along which there flows the liquid to be injected. Inside the box, there are also circuits for controlling the operation of the pump and for monitoring said operation, together with an electrical power supply.

On the front face 12 of the box, there are keys for controlling operation of the pump, given reference 22, and preferably also a display element 24. On the back face 14 of the pump box, means are provided for fixing and locking the pump box on a link member which is described below. The fixing means essentially comprise two slideways 30 and 32 that preferably extend lengthwise relative to the box and that are preferably integrally formed in the thickness of the walls of the box. The slideways 30 and 32 are separated by a groove-forming hollow zone 34 in which a locking ramp 36 is formed having a sloping portion 36a facing the engagement inlet of the recess 34, and a portion 36b having a steep face to constitute a locking face.

With reference now to FIGS. 5 to 7, there follows a description of a preferred embodiment of the link member given overall reference 40. As mentioned briefly above, the link member serves to enable various accessories to be fixed to the pump box. In a preferred embodiment, the link member 40 is constituted by an elongate piece 42 having a substantially plane portion 44 in which an opening of generally rectangular shape 46 is formed. A tongue 48 is mounted in said opening to pivot relative to the plate 44 about two pivot axes 50 and 52 disposed between a free end 54 and a locking end 56 of the tongue 48. In a preferred embodiment, the entire link member 40 is made of a plastics material, and the tongue 48, the pivot axes 50 & 52, and the plate 44 are integrally formed, thereby defining not only the pivot axis 50, 52 but also resilient return means for putting the tongue into the plane of the plate 44. The plate 44 has a side wall 58 from which there project two ribs 60 and 62 disposed on opposite sides of the plate 44. It will be understood that the ribs 60 and 62 are located in a plane that is offset relative to that of the plate 44. The ribs 60 and 62 are configured so as to enable them to slide in the slideways 30 and 32 of the box 10 when the link member is placed facing the back face of the pump box. The locking end 56 of the tongue 48 has a locking projection 64 which is disposed facing the groove 34 in the back face of the pump box. Consequently, when the link member is engaged against the back face of the pump box, the locking projection 64 slides in the groove 34 and can go beyond the locking ramp 36. By co-operation between the slideways 30, 32 and the ribs 60, 62, and also by co-operation between the locking projection 64 and the locking ramp 36, the link member 40 can be secured to the back face of the pump box in temporary manner. It will be understood that by pushing on the outer face of the end 54 of the tongue 48, it is possible to lift the locking projection 64, thereby enabling the link member 40 to be released from the pump box. Thus, because of the way in which the pump body is linked to the link member, these two pieces can be separated very easily and the pump can have any external fixing member removed therefrom.

The top face 44a of the plate 44 also constitutes a zone on which an accessory can be fixed. For this purpose, the plate includes fixing holes such as 66, 68, and 69. It should be observed that at least a portion of said fixing zone, e.g. the portion defined by the holes 66 or the set of holes 66 and 68, leaves the control end 54 of the tongue 48 free so as to enable the link member to be unlocked from the pump box.

As already mentioned, various accessories can be fixed to the fixing zone of the link member 40 depending on the way in which the pump is used. FIGS. 8 and 9 show a first accessory which constitutes a hook or clip. This hook is constituted by a substantially rectangular resilient plate or blade 70 having a free end 72 and including at its second end 74 an extension 76. The free face 76a of the extension constitutes a second fixing zone for the accessory 70. The face 76a has blind tapped holes such as 78 facing holes 66 in the link member. By engaging screws such as 80 in the holes 66 and the blind holes 78, the end 74 of the flexible blade 70 can be secured to the link member. The blade 70 co-operating with the top face 44a of the link member 40 thus constitutes a hook that can, for example, be engaged on the belt of a patient who needs to wear the pump 10.

With reference now to FIG. 10, there is described another example of an accessory that can be fixed to the pump box. This is a piece 90 for fixing the pump 10 on a bracket. The piece 90 comprises a jaw 92 fitted with a clamping screw 94. The jaw 92 is disposed around the bracket (not shown in FIG. 10) and the screw 94 enables the jaw 92 to be clamped onto the bracket. The jaw 92 has a fixing block 96 pivotally mounted thereon by means of a ball-and-socket system. The block has a sloping face that constitutes the fixing zone of the accessory. In FIG. 10, a link member 40 is shown fixed via its top face 44a to the face 98 of the block 96 by means of screws (not shown in the figure) which are engaged in the holes 66 and 68 of the link member 40. The face 98 of the block preferably leaves the control end 54 of the tongue 48 free. The link member 40 can then be locked to the pump box 10 in the manner explained above.

Because of the hinge between the block 96 and the jaw 92, it is possible to rotate the pump box so as to give it any desired orientation such that its control face is easily accessible, particularly when it is fixed on the vertical bar of a tripod support and/or on a horizontal bar of the bed of a patient.

FIGS. 11 and 12 show another accessory that can be associated with the pump 10 by means of the link member 40. This accessory is constituted by a case in the form of a bag or rigid pocket whose bottom portion 102 is designed to receive a flexible pouch (not shown in the figure) containing the liquid to be injected. The rigid top portion 104 is designed to receive the pump box 10. The box 10 is fixed to the wall 106 of the case 100 by means of the above-described link member 40. The member 40 is fixed to the periphery of an opening 110 formed in the wall 106 so that the ribs 60 and 62 lie inside the case and the top face 44a faces outwards. On this face, the holes 66 and 68 can be used to fix a clip 70 of the type described with reference to FIGS. 8 and 9 in order to enable the case 100 to be hooked onto the belt of the user.

FIG. 13 shows the pump box 10 mounted in the case 100. It also shows the portion 112 of the tube 20 connected to the bag contained in the case 100, and the portion 114 of the tube whose other end is fixed to an injection needle or cannula.

Naturally, numerous other accessories could be fixed in temporary manner to the pump box by means of the single link member 40.

In particular, the accessory fixed on the link member 40 may be a male or female fastener element suitable for co-operating, e.g. by snap-fastening, with an additional female or male fastener element. The additional fastener element may be a specific fixing piece.

We claim:

1. A portable pump assembly comprising a pump mounted in a box and a plurality of distinct accessories fixable on said pump box, wherein:

said pump box (10) has both a control face (12) and a fixing face (14) that is distinct from the control face, said fixing face including first mechanical fixing means (30, 32) and non-moving first locking means (36);

said pump box further includes a single link member (40) having a top face (44a) and second mechanical fixing means (60, 62) disposed in a plane offset from the top face, said first and second mechanical fixing means forming a rib-and-slideaway system, and with moving second locking means (48, 64) such that when the first and second mechanical fixing means co-operate mutually, the first and second locking means (48, 64) also co-operate to secure said link member of said box, and the top face including a first fixing zone and a control element (54) for unlocking the second locking means;

each accessory (70, 90, 100) includes a second fixing zone suitable for engaging at least a portion of said first fixing zone; and each accessory further includes fixing means (80) for fixing said second fixing zone on at least a portion of said first fixing zone.

2. A portable pump assembly according to claim 1, characterized in that the first and second mechanical fixing means comprise slideway-forming means (30, 32) secured to one of the elements constituted by the box (10) and the link member (40), and ribs (60, 62) suitable for co-operating with said slideway-forming means and secured to the other element.

3. A portable pump assembly according to claim 1, characterized in that the non-moving first locking means comprise a locking ramp (36) formed in the fixing face of the box (10), and in that the moving second locking means comprise a tongue (48) mounted to pivot relative to said link member (40, 44), said tongue including a first end (56) provided with a locking member (64) suitable for cooperating with the first locking means when said first and second fixing means are co-operating, and a second end (54) constituting said control element.

4. A portable pump assembly according to claim 1, characterized in that said first and second fixing zones respectively comprise orifices (66, 68, 69, 78) and tapped holes, and in that the fixing means comprise screws (80).

5. A pump assembly according to claim 1, characterized in that said control element (54) for the second locking means is external to at least a portion of said first fixing zone.

6. A portable pump assembly according to claim 1, characterized in that one of said accessories is constituted by a resilient blade (70) having a free first end (72) and a second end secured to an extension (76) projecting from a face of said blade, the free end (76a) of said extension forming said second fixing zone, thereby enabling said accessory to constitute a hook when fixed on said link member.

7. A portable pump assembly according to claim 1, characterized in that one of said members is a fixing piece (90) for fixing to a bracket, said fixing piece comprising a fixing jaw (92) for engaging the bracket and a fixing body (96), said fixing body having a face that forms said second fixing zone.

8. A pump assembly according to claim 7, characterized in that said fixing body (96) is connected to said jaw (92) via a ball-and-socket assembly.

9. A pump assembly according to any one of claims 1 to 6, characterized in that one of said accessories is constituted by a case in the form of a bag (100) having a first portion (102) suitable for receiving a pouch containing the liquid to be injected by means of said pump, and a second portion (104) suitable for receiving said pump (10), said second portion having a wall (106) defining a second fixing zone suitable for co-operating with the first fixing zone of said link member (40).

10. A pump assembly according to any one of claims 1 to 5, characterized in that one of said accessories is constituted by a snap-fastening member suitable for co-operating with the snap-fastening member of an additional accessory.

* * * * *